(12) United States Patent
Campogarrido et al.

(10) Patent No.: US 7,794,735 B2
(45) Date of Patent: Sep. 14, 2010

(54) PATHOGEN FOR BACTERIAL POULTRY DISEASE

(75) Inventors: Raul Campogarrido, Zapopan (MX); Carlos Gonzalez-Hernandez, Tlajomulco de Zúñiga (MX); Vaithianathan Sivanandan, Austin, TX (US); Maria Elena Vazquez, Guadalajara (MX)

(73) Assignee: Boehringer Ingelheim Vetmedica S.A. DE C.V., Guadalajara (MX)

( * ) Notice: Subject to any disclaimer, the term of this patent is extended or adjusted under 35 U.S.C. 154(b) by 221 days.

(21) Appl. No.: 12/392,594

(22) Filed: Feb. 25, 2009

(65) Prior Publication Data

US 2009/0181055 A1    Jul. 16, 2009

Related U.S. Application Data

(63) Continuation of application No. 10/279,732, filed on Oct. 24, 2002, now Pat. No. 7,521,060.

(60) Provisional application No. 60/348,254, filed on Nov. 7, 2001.

(30) Foreign Application Priority Data

Oct. 26, 2001    (DE)    ............... 101 52 307

(51) Int. Cl.
*A61K 39/102* (2006.01)
*A61K 35/00* (2006.01)
*A61K 39/02* (2006.01)
*A61K 39/295* (2006.01)
*C12N 1/20* (2006.01)
*G01N 33/569* (2006.01)

(52) U.S. Cl. ............... 424/255.1; 424/93.4; 424/234.1; 424/200.1; 424/201.1; 435/252.2; 435/7.32

(58) Field of Classification Search .................. None
See application file for complete search history.

(56) References Cited

U.S. PATENT DOCUMENTS 5,849,305 A    12/1998    Briggs et al.
5,855,894 A    1/1999    Brown et al.
6,114,131 A    9/2000    Storm et al.

FOREIGN PATENT DOCUMENTS

CA    2232119 A1    9/1998

OTHER PUBLICATIONS

Oystein et al.; Phenotypic and genotypic characterization of Mannheimia (*Pasteurella*) *haemolytica*-like strains isolated from diseased animals in Denmark; Veterinary Microbiology; 2002; vol. 84; No. 1-2; pp. 103-114.
Christensen et al.; Genetic relationships among avian isolates classified as *Pasteurella haemolytica* '*Actinobacillus salpingitdis*' or *Pasteurella anatis* with proposal of *Gallibacterium anatis* gen. nov., comb. nov. and description of additiional genomospecies with *Gallibacterium* gen. nov; International Journal of Systematic and Evolutional Microbiology; 2003; vol. 53; pp. 275-287.
Bojesen et al.; Detection of *Gallibacterium* spp. in Chickens by Flluorescent 16S rRNA in Situ Hybridization; Journal of Clinical Microbiology; Nov. 2003; vol. 41; No. 11; pp. 5167-5172.
Hacking et al.; *Pasteurella hemolytica* in Pullets and Laying Hens; Avian Diseases; 1974; vol. 3; pp. 483-486.
Frank et al.; Rapid plate agglutination procedure for serotyping *Pasteurella haemolytica*; Journal Clinical Microbiology; 1978; vol. 2; pp. 142-145.
Jaworski et al.; Biovariants of isolates of *Pasteurella* from domestic and wild ruminants; J.Vet. Diagn. Invest.; 1998; vol. 10; pp. 49-55.
Fodor et al.; Serotypes of *Pasteurella haemolytica* and *Pasteurella trehalosi* isolated from farm animals in Hungary; Zentralbl Veterinarmed [B]; May 1999; vol. 46; No. 4; pp. 241-247.
Tabatabai et al.; Conservation of expression and N-terminal sequences of the *Pasteurella haemolytica* 31-kilodalton and *Pasteurella trehalosi* 29-kilodalton periplasmic iron-regulated protein; Clin Diagn Lab Immunol.; Jul. 1999; vol. 6; No. 4; pp. 617-620.
Sneath et al.;*Actinobacillus rossii* sp. nov.,*Actinobacillus seminis* sp. nov., nom. rev.,*Pasteurella bettii* sp. nov.,*Pasteurella lymphangitidis* sp. nov.,*Pasteurella mairi* sp. nov., and*Pasteurella trehalosi* sp. nov; Int J Syst Bacteriol; Apr. 1990; vol. 40; No. 2; pp. 148-153.
Greenspan et al.; Defining epitopes: It's not as easy as it seems; Nature Biotechnology; Oct. 1999; vol. 17; pp. 936-937.
Bowie et al.; Deciphering the Message in Protein Sequences: Tolerance to Amino Acid Substitutions; Science; 1990; vol. 257; pp. 1306-1310.

*Primary Examiner*—Robert A Zeman
(74) *Attorney, Agent, or Firm*—Michael P. Morris; Mary-Ellen M. Devlin; Joyce L. Morrison

(57) ABSTRACT

The invention belongs to the field of animal health and in particular the causative agent of a new bacterial poultry disease, *Gallibacterium*. The invention provides said *Gallibacterium* bacteria, vaccine comprising inactivated *Gallibacterium*, and a method of immunizing to prevent disease in poultry.

4 Claims, 22 Drawing Sheets

(22 of 22 Drawing Sheet(s) Filed in Color)

PATHOGEN FOR BACTERIAL POULTRY DISEASE

RELATED APPLICATIONS

This application is a continuation of application Ser. No. 10/279,732 filed Oct. 24, 2002, now issued as U.S. Pat. No. 7,521,060, which is a nonprovisional of application Ser. No. 60/348,254 filed Nov. 7, 2001, which is expired, which claims priority to German application S/N 101 52 370, filed Oct. 26, 2001.

FIELD OF THE INVENTION

The invention belongs to the field of animal health and in particular the causative agents of a new bacterial poultry disease, *Gallibacterium*. The invention provides said *Gallibacterium* bacteria, a vaccine comprising inactivated *Gallibacterium*, and a method of immunizing chicken to prevent said disease in chicken.

BACKGROUND OF THE INVENTION

During the last decade, intensive poultry farming methods to increase productivity, has resulted in an increase of disease manifestation throughout all major poultry producing countries. This has caused an increasing need for new and better vaccines and vaccination programs to control these diseases. Nowadays, most animals are immunized against a number of diseases of viral and bacterial origin. Examples of viral diseases in poultry are Newcastle Disease, Infectious Bronchitis, Avian Pneumovirus, Fowlpox, Infectious Bursal Disease etc.

Examples of bacterial diseases are Avian Coryza caused by *Haemophilus paragallinarum* (upper respiratory tract), *Bordetella avium* (upper respiratory tract), *Ornithobacterium rhinotracheale* (lower respiratory tract), *Salmonella* infections (digestive tract), *Pasteurella multocida*, which is the causative agent of fowl cholera (septicemic), and *E. coli* infections.

Therefore, the technical problem underlying this invention was to identify a new bacterial poultry disease, to provide the causative agent of said disease and to provide a vaccine to prevent said disease.

BRIEF DESCRIPTION OF THE DRAWINGS

The patent or application file contains at least one drawing executed in color. Copies of this patent or patent application publication with color drawings will be provided by the Office upon request and payment of the necessary fee.

A) From Field Outbreaks

B) Experimental Infection

Figure 1:
FIG. 1) Broilers: Nasal discharge and swollen areas around the eye.
Figure 2:
FIG. 2) Broilers: Haemorrhage in heart and coronary fat.
Figure 3:
FIG. 3) Broilers: Conjuctivitis and inflammation around the eye.
Figure 4:
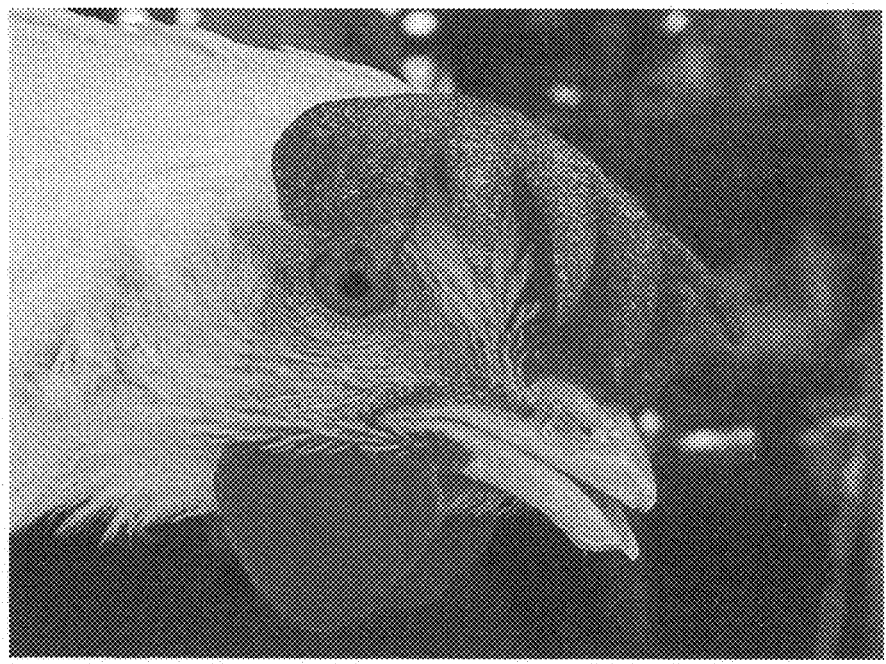
FIG. 4) Layers: Nasal discharge and displaced comb with cyanosis.
Figure 5:
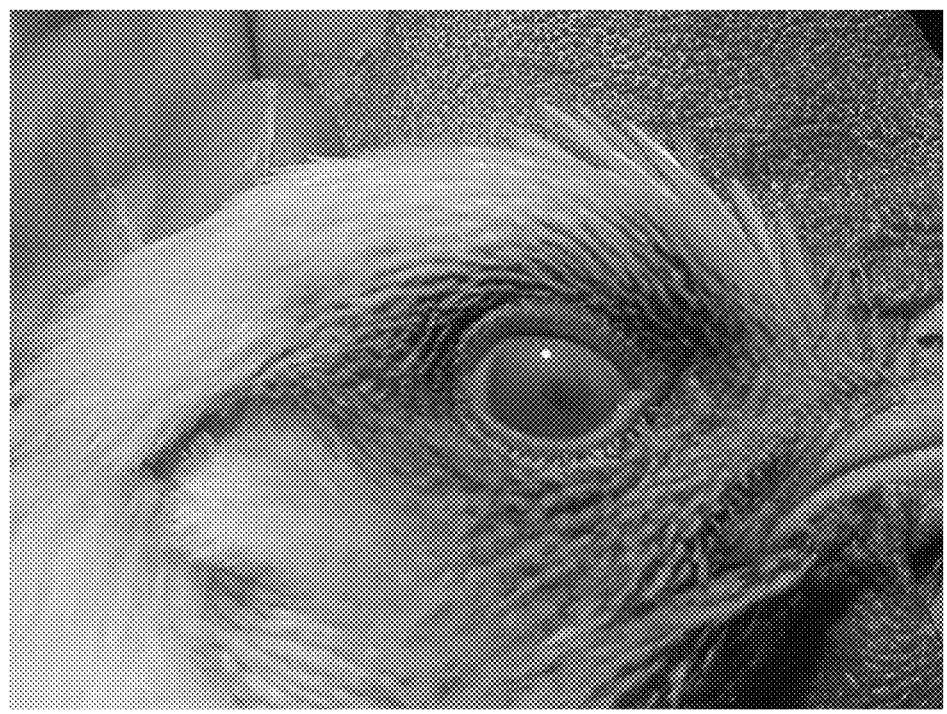
FIG. 5) Layers: Inflammation and haemorrhage around the eye.
Figure 6:
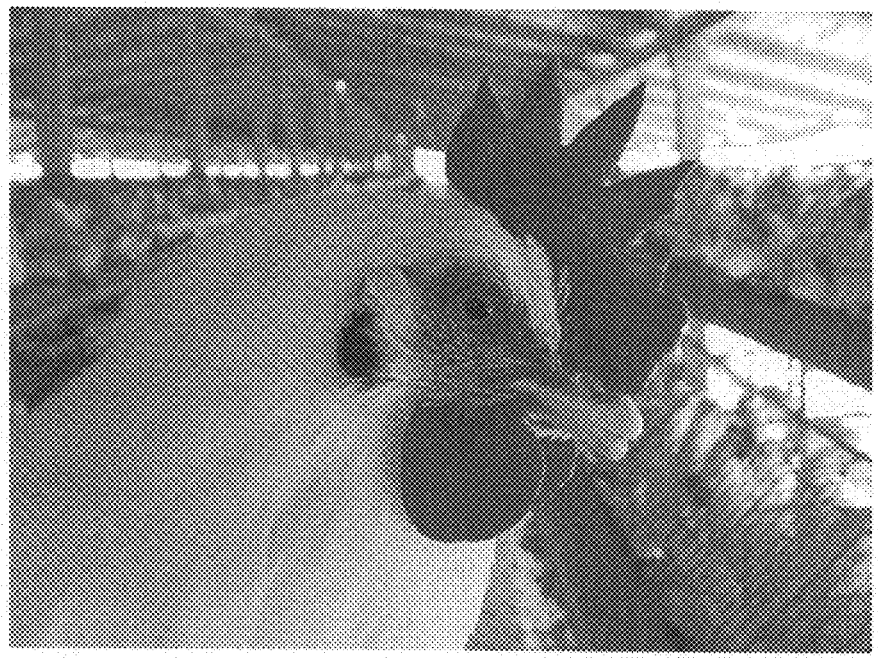
FIG. 6) Layers: Haemorrhage in the dermal tissue behind entrance to auditory orifice.
Figure 7:
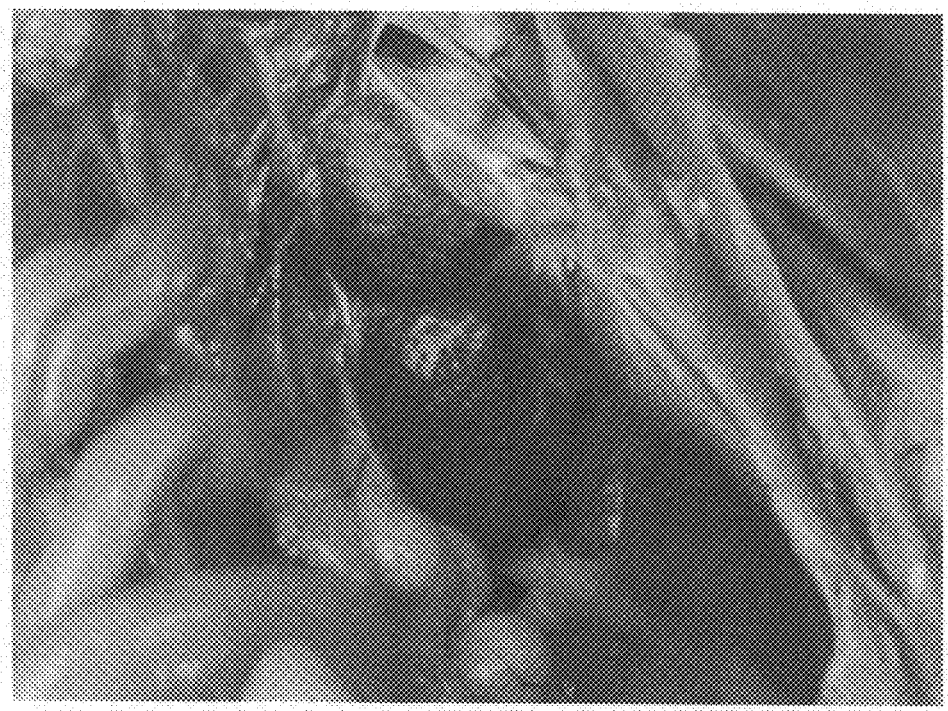
FIG. 7) Layers: Inflammation of kidneys.
Figure 8:
FIG. 8) Layers: Haemorrhages in oviduct.
Figure 9:
FIG. 9) Layers: Deformed ovarian follicles.
Figure 10:
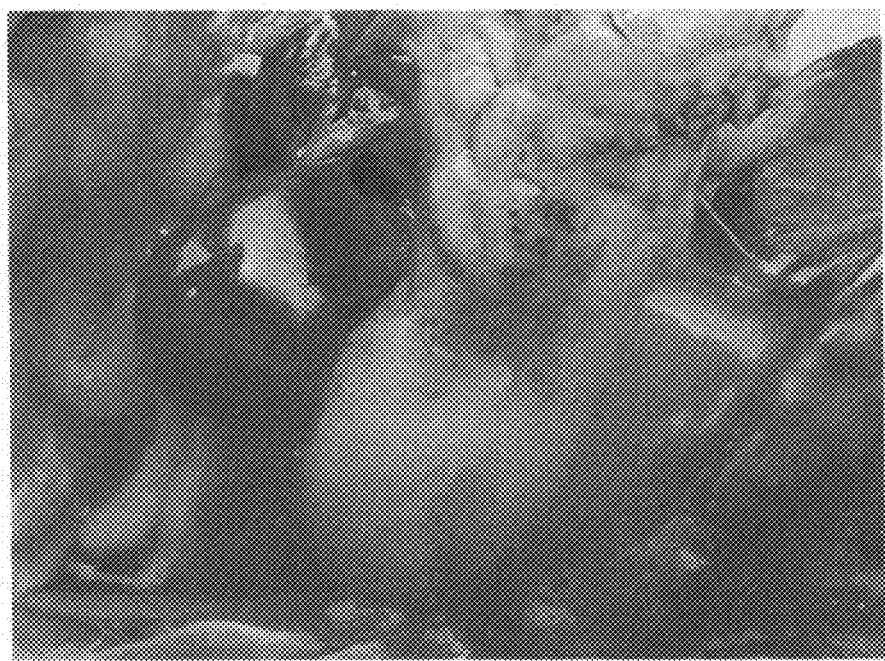
FIG. 10) Layers: Haemorrhage in the junction between proventriculus and gizzard.
Figure 11:
FIG. 11) Layers: Congestion and haemorrhage in oviduct.
Figure 12:

FIG. 12) Layers: Inflammation and haemorrhage in kidney.

Figure 13:
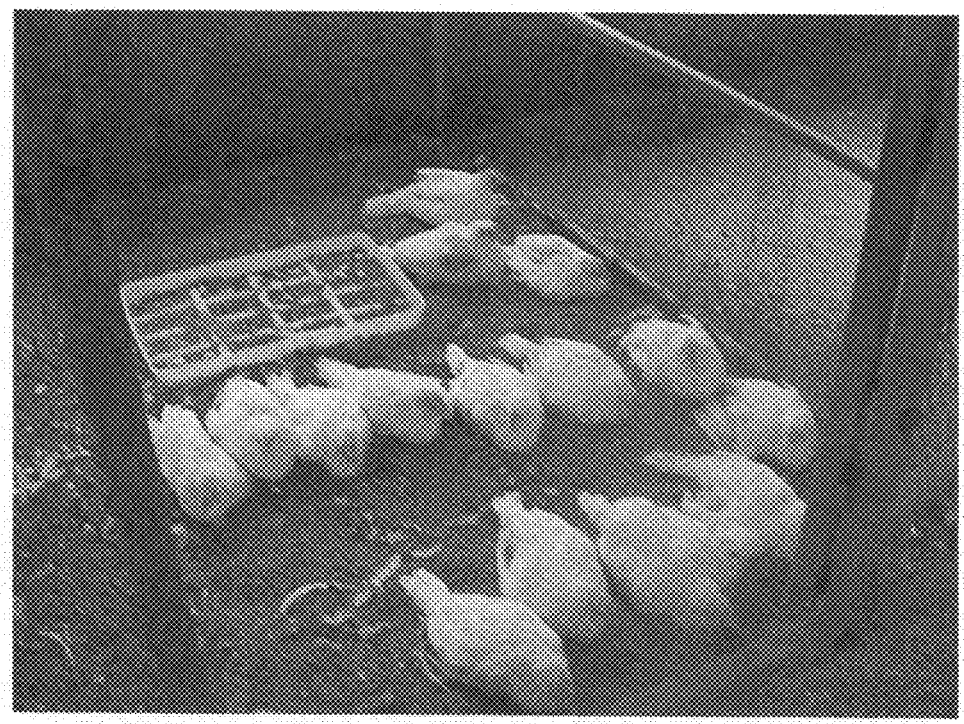

FIG. 13) SPF: Prostration.

Figure 14:

FIG. 14) Layers: Haemorrhage in joint and muscle.

Figure 15:

FIG. 15) Layers: Nasal discharge and pale comb.

Figure 16:
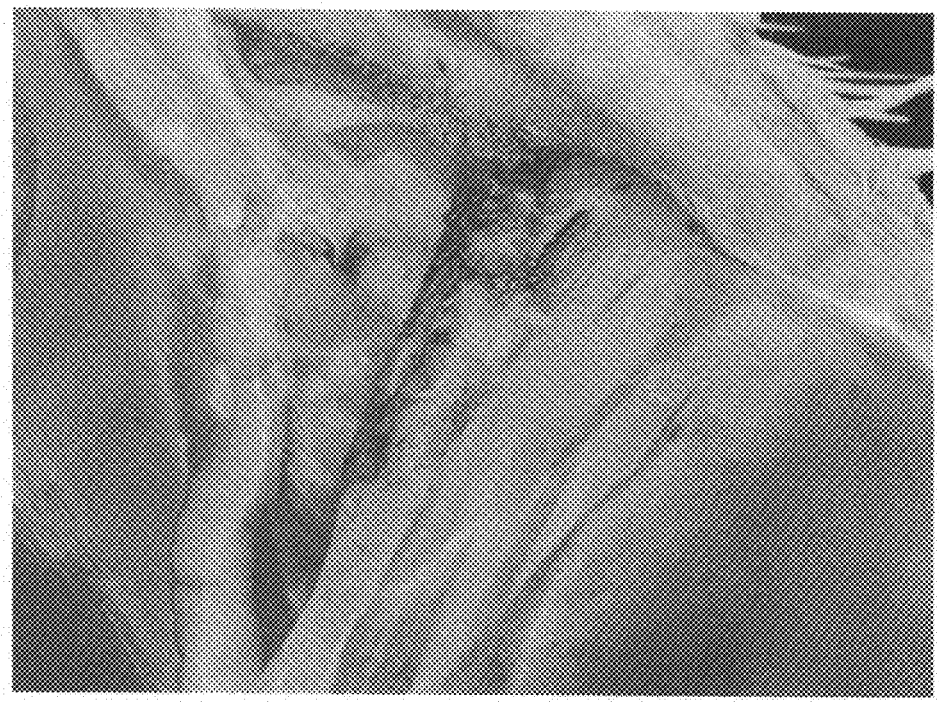

FIG. 16) Layers: Haemorrhage in muscle.

Figure 17:

FIG. 17) SPF: Haemorrhage in heart and coronary fat.

Figure 18:

FIG. 18) Layers: Healthy bird on the left and sick bird on the right with ruffled feathers.

Figure 19:

FIG. 19) Layers: Greenish diarrhea.

Figure 20:

FIG. 20) SPF: Haemorrhage in muscle.

Figure 21:

FIG. 21) SPF: Prostration (locomotive problems) and greenish diarrhea.

Figure 22:

FIG. 22) Layers: Enlarged liver with haemorrhage.

DISCLOSURE OF THE INVENTION

Definitions of Terms Used in the Description

Before the embodiments of the present invention it must be noted that as used herein and in the appended claims, the singular forms "a", "an", and "the" include plural reference unless the context clearly dictates otherwise. Thus, for example, reference to "a *Gallibacterium*" includes a plurality of such *Gallibacterium* bacteria, reference to the "cell" is a reference to one or more cells and equivalents thereof known to those skilled in the art, and so forth. It is irrelevant whether a word is capitalized or not, therefore both "Arabinose" and "arabinose" have the same meaning, unless indicated otherwise. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

Surprisingly, a new bacterial poultry disease has been observed by the present inventors, which occurs primarily in layers and less frequent in broilers. The disease was seen in chicken that had been vaccinated against the bacterium *Haemophilus paragallinarum* (causative agent of avian Coryza), and *Pasteurella multocida* (causative agent of fowl cholera). The symptoms of this new disease differ from the specific symptoms of Coryza. Given the fact that the newly discovered disease clearly shows the clinical signs of a upper respiratory tract infection as described below, *H. paragallinarum* could be ruled out as the causative agent.

The present invention relates in a first embodiment to Gram-negative, facultative anaerobic, pleomorphic rod-shaped bacteria causing a novel disease of the upper respiratory and of the reproductive tract of poultry, wherein said bacteria are selected from *Gallibacterium*.

Said bacteria according to the invention may be isolated from infected trachea, palatine cleft, ovary, liver, heart, kidney and gonads (broilers). They can be identified as *Gallibacterium* according to the invention based on the tests listed below:

| | |
|---|---|
| Beta haemolysis | + |
| Gram stain | − |
| Oxidase | + |
| Catalase | + |
| Urease | − |
| Nitrate | + |
| Indole | − |

The bacterial isolates are preferably purified and biotyped according to the method initially proposed by Christensen et al. (Christensen, H., Bisgaard, M., Bojesen, A. M., Mutters, R., and Olsen, J. E., Genetic relationships among avian isolates classified as *Pasteurella haemolytica*, '*Actinobacillus salpingitidis*' or *Pasteurella anatis* with proposal of *Gallicaterium anatis* gen. nov., comb. nov. and description of additional genomospecies within *Gallibacterium* gen. nov., *Int. J. Syst. Evol. Microbiol.*, 2003, 53, 275-287). Said methods may be applied by the artisan to find out whether bacteria are within the scope of the present invention.

Previously, the bacterial isolates were purified and biotyped according to the method described by Jaworski et al. (Jaworski M. D., D. L. Hunter, A. C. S. Ward. Biovariants of isolates of *Pasteurella* from domestic and wild ruminants. J. Vet. Invest. 1988, 10: 49-55.). This method is also exemplified in the examples. Important method to classify bacteria are DNA-DNA hybridization, REA (restriction enzyme analysis see e.g. J. Clinical Microbiol, 1993, 31: 831-835) and ribotyping. A challenge model to validate Koch's postulates is also exemplified in the examples.

Thus, an important embodiment of the present invention are *Gallibacterium*, wherein said *Gallibacterium* are beta(β)-haemolysis-positive, Gram-negative, oxidase-positive, catalase-positive, urease-negative, nitrate-positive and indole-negative. Preferably, said *Gallibacterium* according to the invention are also MacConkey-positive. Even more preferred, said *Gallibacterium* according to the invention are additionally Glucose-positive, Sucrose-positive, Mannitol-positive, Arabinose-negative, Celobiose-negative, Xylose-positive, Salicin-negative, Ornithine-negative, Esculin-negative, alpha-Fucosidase-negative, beta-Galactosidase-positive. Most preferred are *Gallibacterium* according to the invention, wherein said *Gallibacterium* are also Arabinose-negative and Trehalose-positive. Preferably also, said *Gallibacterium* according to the invention are also beta(β)-Glucosidase-negative or -positive, depending on the biotype. Also most preferred are *Gallibacterium* according to the invention, wherein said *Gallibacterium* are furthermore Arabinose-negative and Trehalose-negative. Preferably also, said *Gallibacterium* according to the invention are also beta-Glucosidase negative.

These characteristic properties of the bacteria according to the invention renders the bacteria according to the invention novel over other known bacterial poultry pathogens (Diseases of Poultry, Tenth Edition, Edited by B. W. Calnek, Iowa State University Press, Iowa, U.S.A. 1997).

Another preferred embodiment of the present invention are *Gallibacterium* according to the invention, wherein said poultry is selected from the group of chicken, turkey, duck, goose, dove, pigeon and quail.

The invention provides a novel type of Gram-negative, facultative anaerobic, pleomorphic rod-shaped bacteria, said novel type of bacteria being characterized by the bacteria deposited at the American Type Culture Collection (ATCC), 1081, University Boulevard, Manassas, Va. 20110-2209, USA, under the following deposit numbers:

ATCC No. PTA-3667 (internal designation BIV-4985);
ATCC No. PTA-3668 (internal designation BIV-AVICOR);
ATCC No. PTA-3669 (internal designation BIV-07990).
The date of deposit was Aug. 22, 2001.

Thus, a most preferred embodiment of the present invention are *Gallibacterium* as deposited at the under accession number ATCC No. PTA-3667. These bacteria are further exemplified in table 3 of example 1.

Another most preferred embodiment of the present invention are *Gallibacterium* as deposited at the under accession number ATCC No. PTA-3668. These bacteria are further exemplified in table 2 of example 1.

Another most preferred embodiment of the present invention are *Gallibacterium* as deposited at the under accession number ATCC No. PTA-3669. These bacteria are further exemplified in table 1 of example 1.

In light of the on-going terminology changes in the art, the strains of the present application were subjected to phenotypical characterization according to Christensen et al. (2003), including gram, urase enzyme activity, motility, cytochrome oxidase activity, and haemolysis. Furthermore, all the strains were hybridized both with *Gallibacterium*-specific probe GAN850, and its inverse and complementary probe, and the *Gallibacterium*-specific probe EUB338 according to Bojesen et al., Detection of *Gallibacterium* spp. In Chickens by Fluorescent 16S rRNA In Situ Hybridization, *J. Clin. Microbiol.*, Vol. 41, No. 11, November 2003, p. 5167-5172. The results from both phenotypic and genotypic characterization indicated that all the strains belonged to genus *Gallibacterium*.

Under the previous method described by Jaworski et al., the results of tests from sections A and B in the examples (Tables 1, 2 and 3) initially indicated that the bacteria BIV-4895; ATCC No. PTA-3667 and BIV-AVICOR; ATCC No. PTA-3668 belonged to the family Pasteurellaceae, genus *Pasteurella* (*Pasteurella trehalosi*, which are Trehalose positive and arabinose negative), while the bacteria BIV-07990; ATCC No. PTA-3669 belonged to the family Pasteurellaceae, genus *Mannheimia* (*Mannheimia haemolytica*, which are Trehalose negative and arabinose negative).

The invention also relates to microbiological culture comprising bacteria according to the invention as disclosed above. The culture may be made by growing said bacteria at a temperature of between 35° and 37° C. The bacteria may be grown under normal atmospheric oxygen pressure. The bacteria can be grown in a variety of different general-purpose bacterial growth promoting media known to the skilled person, e.g. Tryptose Broth (TB), Soy Trypticasein Broth or Brain Heart Infusion broth or any enriched media. The bacteria may also be grown on sheep blood agar incubated at 37° C. for 24 hours.

Various physical and chemical methods of bacterial inactivation are known in the art. Examples of physical inactivation are UV-radiation, X-ray radiation, gamma-radiation and heating. Examples of inactivating chemicals are beta-propiolactone, glutaraldehyde, beta-ethyleneimine and formaldehyde.

Preferably the bacteria according to the invention are inactivated with formaldehyde. Surprisingly, the use of formaldehyde at a final concentration of 0.2% is an excellent method to inactivate the bacteria according to the invention.

Thus, in another important aspect, the invention relates to a method for inactivation of a *Gallibacterium* according to the invention comprising the use of formaldehyde at a final concentration of 0.2%.

Said bacteria according to the invention which are inactivated by the methods disclosed supra and by other methods of inactivating the bacteria known to the skilled person are embodied in the present invention. Therefore, another important aspect are inactivated *Gallibacterium* obtainable by a method according to the invention or by a method known in the art. Preferably, said inactivated *Gallibacterium* according to the invention are selected from the group of ATCC No. PTA-3667, ATCC No. PTA-3668 and/or ATCC No. PTA-3669.

Therefore, another important aspect are live attenuated *Gallibacterium* obtainable by a method known in the art. Preferably, said live attenuated *Gallibacterium* according to the invention are selected from the group of ATCC No. PTA-3667, ATCC No. PTA-3668 and/or ATCC No. PTA-3669. Said *Gallibacterium* according to the invention are attenuated by multiple passages in appropriate culture media or by any other method known in the art.

Inactivated as understood herein means, that the *Gallibacterium* according to the invention are killed without possible replication to cause clinical disease.

Attenuated as understood herein means, that the *Gallibacterium* according to the invention are live bacteria with possible replication but will not cause clinical disease.

Yet another important aspect are fractions or fragments of *Gallibacterium* obtainable by a method known in the art. Said fragments may be prepared by detergent solubilization of *Gallibacterium* according to the invention or by any other method known in the art.

Preferably, said fractions or fragments are purified antigens of said *Gallibacterium* according to the invention. Preferably, said fractions/fragments are outer membrane proteins of *Gallibacterium* according to the invention.

A "fragment" according to the invention is any immunogenic subunit of a said *Gallibacterium* according to the invention, i.e. any polypeptide subset.

Thus, the invention relates to fragments containing at least one antigen of *Gallibacterium* according to the invention. Most preferably, said fragments are containing at least one antigen of bacteria selected from the group of ATCC No. PTA-3667, ATCC No. PTA-3668 and/or ATCC No. PTA-3669. Said fragment may comprise whole bacterial cells of said strain(s), bacterial extracts, Outer Membrane Fractions, bacterial exo- and/or endotoxins, and purified proteins. Antigenic polypeptides or fragments thereof may for example be obtained from purified bacterial proteins or by expression of the corresponding genetic material in some prokaryotic or eukaryotic expression system or by organo-chemical synthesis. Said methods are known to the skilled person.

The invention further relates to live, and/or live attenuated, and/or inactivated *Gallibacterium* according to the invention and/or fractions of said *Gallibacterium* for use in a vaccine.

The invention further provides a vaccine derived from the newly identified bacteria disclosed above. Thus, the invention further relates to a vaccine composition comprising a live, and/or live attenuated, and/or inactivated *Gallibacterium* according to the invention and/or fractions of said *Gallibacterium*.

The term "vaccine" as understood herein is a vaccine for veterinary use comprising antigenic substances and is administered for the purpose of inducing a specific and active or passive immunity against a disease provoked by said *Gallibacterium*. The live or live attenuated *Gallibacterium* according to the invention confer active immunity that may be transferred passively via maternal antibodies against the immunogens it contains and sometimes also against antigenically related organisms. The inactivated *Gallibacterium* according to the invention and/or fractions of said *Gallibacterium* confer passive immunity.

Additional components to enhance the immune response are constituents commonly referred to as adjuvants, like e.g. aluminium hydroxide, mineral or other oils or ancillary molecules added to the vaccine or generated by the body after the respective induction by such additional components, like but not restricted to interferons, interleukins or growth factors.

In a preferred embodiment, said vaccine comprises inactivated bacteria.

Preferably, a vaccine of the invention refers to a vaccine as defined above, wherein one immunologically active component is a live *Gallibacterium*. The term "live vaccine" refers to a vaccine comprising a particle capable of division/multiplication.

Preferably also, a vaccine according to the invention comprises attenuated *Gallibacterium* according to the invention and a pharmaceutically acceptable carrier or excipient. Said vaccine may also be administered as a combined vaccine comprising two or more strains of said live, and/or live attenuated, and/or inactivated *Gallibacterium* according to the invention and/or fractions of two or more strains of said *Gallibacterium*. Most preferably said live, and/or live attenuated, and/or inactivated *Gallibacterium* according to the invention and/or fractions of said *Gallibacterium* in the vaccine are selected from the group of ATCC No. PTA-3667, ATCC No. PTA-3668 and/or ATCC No. PTA-3669.

Preferably also, a vaccine according to the invention comprises inactivated *Gallibacterium* according to the invention and a pharmaceutically acceptable carrier or excipient. Said vaccine may also be administered as a combined vaccine comprising two or more strains of said inactivated *Gallibacterium*

Furthermore, fractions of whole cells may also be used as the relevant immunogen in the vaccine according to the invention. Therefore, preferably a vaccine according to the invention comprises fractions of *Gallibacterium* according to the invention and a pharmaceutically acceptable carrier or excipient. Said vaccine may also be administered as a combined vaccine comprising two or more strains of said inactivated *Gallibacterium*. In particular, the invention relates to vaccines comprising fragments which contain at least one antigen of *Gallibacterium* according to the invention. Most preferably, the invention relates to vaccines comprising fragments which contain at least one antigen of bacteria selected from the group of ATCC No. PTA-3667, ATCC No. PTA-3668 and/or ATCC No. PTA-3669. Said fragment may comprise whole bacterial cells, bacterial extracts, Outer Membrane Fractions, bacterial exo- and/or endotoxins, and purified proteins. Antigenic polypeptides or fragments thereof may for example be obtained from purified bacterial proteins or by expression of the corresponding genetic material in some prokaryotic or eukaryotic expression system or by organo-chemical synthesis. Said methods are known to the skilled person.

Preferably, the vaccine according to the invention also comprises an adjuvant. Therefore, the invention further relates to a vaccine composition according to the invention, further comprising one or more suitable adjuvant(s) and/or excipient(s) and/or carrier(s).

Adjuvants as used herein comprise substances that boost the immune response of the injected animal. A number of different adjuvants are known in the art. Adjuvants as used herein include Freund's Complete and Incomplete Adjuvant, vitamin E, non-ionic block polymers, muramyldipeptides, Quil A, mineral and non-mineral oil, vegetable oil, and Carbopol (a homopolymer). In a preferred embodiment, the vaccine according to the invention bacterin comprises a water-in-oil emulsion adjuvant. Said vaccine is also called a bacterin comprising inactivated (killed) bacteria according to the invention and a water-in-oil emulsion adjuvant. Other ways of adjuvating the bacteria known to the skilled person are also embodied in the present invention.

Also preferably, the vaccine according to the invention may comprise one or more suitable emulsifiers, e.g. Span or Tween.

Preferably also, said live, and/or live attenuated, and/or inactivated *Gallibacterium* according to the invention and/or fractions of said *Gallibacterium* in the vaccine are selected from the group of ATCC No. PTA-3667, ATCC No. PTA-3668 and/or ATCC No. PTA-3669.

Preferably, the vaccine in the present invention comprises at least one antigen of bacteria selected from the group of ATCC No. PTA-3667, ATCC No. PTA-3668 and/or ATCC No. PTA-3669. Said vaccine may comprise whole bacterial cells of said strain(s), bacterial extracts, Outer Membrane Fractions, bacterial exo- and/or endotoxins, and purified proteins. Antigenic polypeptides or fragments thereof may for example be obtained from purified bacterial proteins or by expression of the corresponding genetic material in some prokaryotic or eukaryotic expression system or by organo-chemical synthesis. Said methods are known to the skilled person.

Most preferably, the invention further relates to a vaccine composition according to the invention, further comprising at least one other antigen from a virus or microorganism pathogenic to poultry. Preferably, said antigen is in the form of live, attenuated or inactivated viruses or microorganisms or fragments thereof. Said fragment may comprise whole bacterial cells or viral particles, bacterial extracts, viral antigens, viral subunits, Outer Membrane Fractions, bacterial exo- and/or endotoxins, and purified proteins. Antigenic polypeptides or fragments thereof may for example be obtained from purified bacterial proteins or by expression of the corresponding genetic material in some prokaryotic or eukaryotic expression system or by organo-chemical synthesis. Said methods are known to the skilled person.

Most preferably, the invention further relates to a vaccine composition according to the invention, further comprising at least one other antigen from a virus or microorganism pathogenic to poultry, wherein said virus or microorganism is selected from, but not restricted to, the group consisting of Infectious Bronchitis Virus, Newcastle Disease Virus, Infectious Bursal Disease Virus (disease: Gumboro), Chicken Anaemia agent, Avian Reovirus, *Mycoplasma gallisepticum, Avian Pneumovirus, Haemophilus paragallinarum* (disease: Coryza), Chicken Poxvirus, Avian Encephalomyelitis virus, *Pasteurella multocida* and *E. coli*.

A "pharmaceutical composition" essentially consists of one or more ingredients capable of modifying physiological e.g. immunological functions of the organism it is administered to, or of organisms living in or on the organism. The term includes, but is not restricted to antibiotics or antiparasitics, as well as other constituents commonly used to achieve certain other objectives like, but not limited to, processing traits, sterility, stability, feasibility to administer the composition via enteral or parenteral routes such as oral, intranasal, intravenous, intramuscular, subcutaneous, intradermal or other suitable route, tolerance after administration, controlled release properties. Thus, in another important aspect of the invention the invention relates to a pharmaceutical composition comprising a live, and/or live attenuated, and/or inactivated *Gallibacterium* according to the invention and/or fractions of said *Gallibacterium*.

The invention relates to a method of treating a *Gallibacterium*-infected animal (e.g. the live bacteria as described above) belonging to the group of poultry wherein said live, attenuated, inactivated *Gallibacterium* and/or fractions and/or fragments thereof according to the invention as described supra, are administered to the poultry animal in need thereof at a suitable doses as known to the skilled person and the reduction of symptoms caused by said *Gallibacterium* infection is monitored. Said treatment preferably may be repeated.

Yet another important embodiment is a method of immunizing poultry against the disease of the respiratory and reproductive tract caused by a *Gallibacterium* (e.g. the live bacteria as described above) comprising administration of an immunologically effective amount of a vaccine according to the invention and the reduction of symptoms caused by said *Gallibacterium* infection is monitored.

Another important embodiment is the use of an inactivated *Gallibacterium* according to the invention and/or live *Gallibacterium* according to the invention and/or live attenuated *Gallibacterium* according to the invention and/or fragments or fractions of said *Gallibacterium* according to the invention in the manufacture of a vaccine for the prophylaxis of *Gallibacterium* infections.

The invention also relates to a method of diagnosis of a disease caused by comprising the steps of obtaining a sample from poultry, wherein said sample is selected from the group of blood, serum, plasma, tissue scrapings, washings, swabs, tissue, analysing said sample for the presence of *Gallibacterium* according to the invention.

In a preferred embodiment the presence of *Gallibacterium* is determined by an immune test. An immune test uses monoclonal antibodies or polyclonal antisera specific to *Gallibacterium*. The generation of monoclonal antibodies is known in the art (Kearney, J. F., Radbruch A., Liesegang B., Rajewski K. A new mouse myeloma cell line that has lost immunoglobulin expression but permits construction of antibody-secreting hybrid cell lines. J. Immunol. 1979, 123: 1548-1550., Köhler, G., Milstein, C. Continuous culture of fused cells secreting antibody of predefined specifity. Nature 1975, 265: 495-497.). Immune tests include the methods of detection known in the art such as the ELISA test (enzyme-linked immuno-sorbent assay) or the so-called sandwich-ELISA test, dot blots, immunoblots, radioimmuno tests (radioimmunoassay RIA), diffusion-based Ouchterlony test or rocket immunofluorescent assays) or agglutination tests (rapid plate or micro-plate agglutination tests). Another immune test is the so-called Western blot (also known as Western transfer procedure or Western blotting). The purpose of Western blot is to transfer proteins or polypeptides separated by polyacrylamide gel electrophoresis onto a nitrocellulose filter or other suitable carrier and at the same time retain the relative positions of the proteins or polypeptides obtained from the gel electrophoresis. The Western blot is then incubated with an antibody which specifically binds to the protein or polypeptide under consideration. These methods of detection can be used by the average skilled person to perform the invention described herein. Literature references in which the skilled person can find the above-mentioned methods and other detection methods are listed as follows: *An Introduction to Radioimmunoassay and Related Techniques*, Elsevier Science Publishers, Amsterdam, The Netherlands (1986); Bullock et al., *Techniques in Immunocytochemistry*, Academic Press, Orlando, Fla. Vol. 1 (1982), Vol. 2 (1983), Vol. 3

(1985); Tijssen, *Practice and Theory of Enzyme Immunoassays: Laboratory Techniques in Biochemistry and Molecular Biology*, Elsevier Science Publishers, Amsterdam, The Netherlands (1985).

In another, most particular embodiment, the sample as disclosed supra is incubated with antibodies which are specific to *Gallibacterium* and the antigen/antibody complex thereby formed is determined.

In a particularly preferred embodiment of the method according to the invention, the presence of *Gallibacterium* in a sample as disclosed supra is determined by molecular biology methods. Molecular biology methods as used herein means detection methods which include, for example, polymerase chain reaction (PCR), reverse transcriptase polymerase chain reaction (RT-PCR) or may be Northern or Southern blots which the skilled person can find in the standard reference books (e.g. Sambrook et al. (1989) Molecular Cloning: A Laboratory Manual, $2^{nd}$ ed., Cold Spring Harbor Laboratory Press, Cold Spring Harbor, N.Y. and Bertram, S, and Gassen, H. G. Gentechnische Methoden, G. Fischer Verlag, Stuttgart, New York, 1991).

The invention also includes a diagnostic test kit according to the invention which is characterised in that it contains all the necessary elements for detecting *Gallibacterium*.

A diagnostic test kit is a collection of all the components for carrying out a method of diagnosis according to the invention. Some examples (not an exhaustive list) of other elements for performing a method according to the invention include containers such as 96-well plates or microtitre plates, test tubes, other suitable containers, surfaces and substrates, membranes such as nitrocellulose filter, washing reagents and buffers. A diagnostic test kit may also contain reagents which may detect bound antibodies, such as for example labelled secondary antibodies, chromophores, enzymes (e.g. conjugated with antibodies) and the substrates thereof or other substances which are capable of binding antibodies.

The invention further relates to a diagnostic test kit according to the invention which is characterized in that it contains all the necessary elements for carrying out a PCR or RT-PCR to detect *Gallibacterium*-specific DNA or RNA. Said kit may contain, but is not limited to in addition to test tubes or 96-well plates or microtitre plates, other suitable containers, surfaces and substrates, membranes such as nitrocellulose filters, washing reagents and reaction buffers (which may vary in pH and magnesium concentrations), sterile water, mineral oil, BSA (bovine serum albumin), $MgCl_2$, $(NH_4)_2SO_4$, DMSO (dimethylsulphoxide), mercaptoethanol, nucleotides (dNTPs), enzymes such as Taq-polymerase and reverse transcriptase and, as the DNA matrix, the DNA or cDNA specific for *Gallibacterium*, oligonucleotides specific for a *Gallibacterium* DNA or RNA, control template, DEPC-water, DNAse, RNAse and further compounds known to the skilled artisan. Oligonucleotides according to the invention are short nucleic acid molecules from about 15 to about 100 nucleotides long, which bind under stringent conditions to the nucleic acid sequence which is complementary to a *Gallibacterium* protein. By stringent conditions the skilled person means conditions which select for more than 85%, preferably more than 90% homology (cf. Sambrook et al. (1989) Molecular Cloning: A Laboratory Manual, $2^{nd}$ ed., Cold Spring Harbor Laboratory Press, Cold Spring Harbor, N.Y. and Bertram, S, and Gassen, H. G. Gentechnische Methoden, G. Fischer Verlag, Stuttgart, New York, 1991).

The following examples serve to further illustrate the present invention; but the same should not be construed as limiting the scope of the invention disclosed herein.

Example 1

Field Disease Outbreaks Associated with *Gallibacterium*

Clinical Signs

From Field Observations

| Layers | Broilers |
|---|---|
| Mild upper respiratory/reproductive | Severe upper respiratory/reproductive |
| Age: 22 weeks of age | Age: 7 weeks |
| Nasal discharge | Sneezing with rales |
| Swollen areas around the eye | Swollen head |
| Low feed consumption | Low feed consumption |
| Whitish diarrhea | Depression |
| Decreased egg production | Non uniform growth |
| Low mortality | Ruffled feathers |
| Comb displaced | Prostration |
| Cyanosis of comb | Mortality 8% |

| Gross Lesions | |
|---|---|
| Ovarian atrophy with haemorrhages and regression | Haemorrhages in gonads |
| Ovarian follicles deformed | Upper part of trachea with haemorrhages |
| Enlarged liver | Enlarged liver with haemorrhages |
| Inflammation of kidneys | Airsacculitis |
| Haemorrhages in abdominal fat | Enlarged spleen with haemorrhages |
| Haemorrhages in thoracic cavity | Haemorrhages in muscle |
| Haemorrhages in oviduct | Haemorrhages in the heart and hydropericardium |
| Haemorrhages of coronary fat | Haemorrhages in the thoracic cavity |

Three strains of a novel type of Gram-negative, facultative anaerobic, pleomorphic rod-shaped bacteria, were deposited at the American Type Culture Collection (ATCC), 1081, University Boulevard, Manassas, Va. 20110-2209, USA, under deposit number: ATCC No. PTA-3667 for BIV-4985; ATCC No. PTA-3668 for BIV-AVICOR, and ATCC No. PTA-3669 for BIV-07990. The date of deposit was Aug. 22, 2001.

The deposited bacteria were typed according to standard determination methods, using Bergey's Manual of Systematic Bacteriology Volume 1 (1984. Williams and Wilkins, 428 East Preston Street. Baltimore, USA.)

Table 1

BIV-07990; ATCC No. PTA-3669

Macroscopic Morphology

Colonies grown on Sheep Blood Agar for 24 hours, range from 1.0 to 1.5 mm in diameter, bright translucent, low convex, smooth and creamy, β hemolysis.

Microscopic Morphology

Gram-negative, non-motile, pleomorphic rods, often exhibit bipolar staining.

Biochemical and Other Tests

Section A

| TEST | REACTION |
| --- | --- |
| Oxidase | + |
| Catalase | + |
| Indole | − |
| Glucose | + |
| Sucrose | + |
| MacConkey | + |
| Urease | − |
| Nitrate | + |

Section B

| | |
| --- | --- |
| Maltose | + |
| Mannitol | + |
| Arabinose | − |
| Celobiose | − |
| Sorbitol | + |
| Xilose | + |
| Treahalose | − |
| Salicin | − |
| Ornithine | − |
| Esculine | − |
| β Glucosidase | − |
| α-Fucosidase | − |
| β Galactosidase | + |

Table 2

BIV-AVICOR; ATCC No. PTA-3668
  Macroscopic Morphology
  Colonies grown on Sheep Blood Agar for 24 hours, range from 1.0 to 1.5 mm in diameter, bright translucent, low convex, smooth and creamy, β hemolysis.
  Microscopic Morphology
  Gram-negative, non-motile, pleomorphic rods, often exhibit bipolar staining.
  Biochemical and Other Tests
  Section A

| TEST | REACTION |
| --- | --- |
| Oxidase | + |
| Catalase | + |
| Indole | − |
| Glucose | + |
| Sucrose | + |
| MacConkey | + |
| Urease | − |
| Nitrate | + |

Section B

| | |
| --- | --- |
| Maltose | + |
| Mannitol | + |
| Arabinose | − |
| Celobiose | − |
| Sorbitol | + |
| Xylose | + |
| Trehalose | + |
| Salicin | − |
| Ornithine | − |
| Esculin | − |
| β Glucosidase | +α |
| α-Fucosidase | − |
| β Galactosidase | + |

α80% are positive

Table 3

BIV-4895; ATCC No. PTA-3667
  Macroscopic Morphology
  Colonies grown on Sheep Blood Agar for 24 hours, range from 1.0 to 1.5 mm in diameter, bright translucent, low convex, particulate and dry, β hemolysis.
  Microscopic Morphology
  Gram-negative, non-motile, pleomorphic rods, often exhibit bipolar staining.
  Biochemical and Other Tests
  Section A

| TEST | REACTION |
| --- | --- |
| Oxidase | + |
| Catalase | + |
| Indole | − |
| Glucose | + |
| Sucrose | + |
| MacConkey | + |
| Urease | − |
| Nitrate | + |

Section B

| | |
| --- | --- |
| Maltose | − |
| Mannitol | + |
| Arabinose | − |
| Celobiose | − |
| Sorbitol | + |
| Xylose | + |
| Trehalose | + |
| Salicin | − |
| Ornithine | − |
| Esculin | − |
| β Glucosidase | − |
| α-Fucosidase | − |
| β Galactosidase | + |

Identification of the Causative Agent

Bacteria were isolated from infected trachea, palatine cleft, ovary, liver, heart, kidney and gonads (broilers). They are identified as *Gallibacterium*.

| | |
| --- | --- |
| Beta haemolysis | + |
| Gram stain | − |
| Oxidase | + |
| Catalase | + |
| MacConkey | + |
| Urease | − |
| Nitrate | + |
| Indole | − |

Initial Biotyping:

Bacterial isolates were initially purified and biotyped according to the method described by Jaworski et al. (1). Three different biotypes (4, 2, 1) were identified. Briefly, from the purified isolates, a single colony was inoculated into tubes containing 3 ml of Tryptose Broth and incubated at 37° C. for 8 hours. A loop of inoculum (20 μl) from the tube was then transferred into another tube containing 3 ml of 1% sugar to be tested and incubated for 7 days at 37° C. before results were recorded Initial Challenge Model:

Following purification of the bacteria, isolates were grown in tryptose media to obtain large quantities of pure pathogens. In order to validate Koch postulates, 3 different groups (20 birds per group) of specific pathogen free (SPF) chicken 13 weeks of age were infected with each biotype (0.2 ml/bird; $3\times10^8$ CFU/ml) by intravenous route. The birds were observed daily for 3 days for morbidity and mortality. At the end of the $3^{rd}$ day, all birds were sacrificed, post-mortem lesions recorded and organ samples (liver and gonads) were collected for re-isolation. Post-mortem lesions of birds that died were also recorded.

Biotyping According to Christensen et al.

In light of the on-going terminology changes in the art, the strains of the present application were subjected to phenotypical characterization according to Christensen et al. (2003), including gram, urase enzyme activity, motility, cytochrome oxidase activity, and haemolysis. Furthermore, all the strains were hybridized both with *Gallibacterium*-specific probe GAN850, and its inverse and complementary probe, and the *Gallibacterium*-specific probe EUB338 according to Bojesen et al., Detection of *Gallibacterium* spp. In Chickens by Fluorescent 16S rRNA In Situ Hybridization, *J. Clin. Microbiol.*, Vol. 41, No. 11, November 2003, p. 5167-5172. The results from both phenotypic and genotypic characterization indicated that all the strains belonged to genus *Gallibacterium*.

Results

Clinical signs: Prostration, Lameness, Displaced comb, Ruffled feathers, Cyanosis at the tip of the comb.

Lesions:

| Lesion | BIV-4895 (Biotype 4) | BIV-Avicor (Biotype 2) | BIV-07990 (Biotype 1) |
|---|---|---|---|
| Heart edema | 73% | 37% | 90% |
| Heart haemorrhages | 90% | — | 70% |
| Haemorrhages in coronary fat | 90% | 37% | 50% |
| Pericarditis | 73% | 46% | 30% |
| Haemorrhages in thoracic cavity | — | 19% | 40% |
| Haemorrhages in ovary | 64% | 9% | 20% |
| Inflammation of kidneys | 64% | 46% | 60% |
| Haemorrhages in kidneys | 55% | 46% | 20% |
| Enlarged liver with haemorrhages | — | 73% | — |
| Airsacculitis | 64% | — | — |
| Haemorrhages in muscle | — | 37% | — |
| Mortality | 46% | 19% | — |

Example II

Growth of the bacteria according to the invention, preparation of the vaccine and vaccination of SPF birds.

Strains were grown on Tryptose Broth (TB). Harvest was done at logarithmic growth phase around 6-8 hours post-inoculation depending on the strain. Plate count was made in sheep blood agar for titration. Colony forming units per mililiter (CFU/ml) was determined using 1:10 dilutions of the harvest. Cells were killed by adding formaldehyde to a final concentration of 0.2%. Following a sterility check of this suspension, a minimal titer of $10^8$ CFU/ml was added to the final vaccine.

The vaccine was prepared by mixing the two strains (BIV-4895, ATCC No. PTA-3667 and BIV-AVICOR, ATCC No. PTA-3668) and oil-adjuvant (a water-in-oil emulsion on the basis of a mineral oil with a ratio of 60% oil/40% water) to a minimal concentration of 107.0 CFU/strain/ml.

Specific pathogen free (SPF) chicken were vaccinated at 2, 5 and 9 weeks of age by injection of 0.5 ml of the vaccine subcutaneously halfway down the neck.

Example III

Preparation of challenge strains and challenge of vaccinated and control groups.

Bacterial strains BIV-4895, ATCC No. PTA-3667 and BIV-AVICOR, ATCC No. PTA-3668, were grown on sheep blood agar for 24 hrs. at 37° C. The cells were harvested in Tryptose Broth (TB) until a suspension with an Optical Density of 2.0 was obtained, using a spectrophotometer at wavelength of 540 nm. For challenge, preparations were made that contain the following number of cells in the final challenge-volume:

$3\times10^9$ CFU/ml BIV-AVICOR; ATCC No. PTA-3668

$1.45\times10^{10}$ CFU/ml BIV-4895; ATCC No. PTA-3667

At 13 weeks of age, 20 vaccinated and 20 non-vaccinated birds were challenged by intravenous route of 0.2 ml of the inoculum (at least $10^{8.0}$ CFU/bird). Birds were observed for 3 days for morbidity and mortality. After three days of observation all the remaining birds were sacrificed and re-isolation of the bacteria from liver and gonads were made from each bird. Post-mortem lesions of birds that died were also recorded.

Results

| Group of birds | Challenge inoculum | Mortality + Reisolation | Protection % |
|---|---|---|---|
| Control Negative | N/A | 0 | N/A |
| Control Positive | ATCC No.PTA-3667 | 77 | 23 |
| Control Positive | ATCC No.PTA-3668 | 54 | 46 |
| Vaccinated | ATCC No.PTA-3667 | 0 | 100 |
| Vaccinated | ATCC No.PTA-3668 | 5 | 95 |

Example IV

Growth of the bacteria according to the invention, preparation of the vaccine and vaccination of SPF birds.

Strains were grown on Tryptose Broth (TB). Harvest was done at logarithmic growth phase around 6-8 hours post-inoculation depending on the strain. Plate count was made in sheep blood agar for titration. Colony forming units per mililiter (CFU/ml) was determined using 1:10 dilutions of the harvest. Cells were killed by adding formaldehyde to a final concentration of 0.2%. Following a sterility check of this suspension, a minimal titer of $10^8$ CFU/ml was added to the final vaccine.

The vaccine was prepared by mixing the three strains (BIV-4895, ATCC No. PTA-3667; BIV-AVICOR, ATCC No. PTA-3668 and BIV-07990, ATCC No. PTA-3669) and oil-adjuvant (a water-in-oil emulsion on the basis of a mineral oil with a ratio of 60% oil/40% water) to a minimal concentration of $10^{7.0}$ CFU/strain/ml.

Specific pathogen free (SPF) chicken were vaccinated at 2, 5 and 9 weeks of age by injection of 0.5 ml of the vaccine subcutaneously halfway down the neck.

Example V

Preparation of challenge strains and challenge of vaccinated and control groups.

Bacterial strains BIV-4895, ATCC No. PTA-3667; BIV-AVICOR, ATCC No. PTA-3668 and BIV-07990, ATCC No. PTA-3669, were grown on sheep blood agar for 24 hrs. at 37°

C. The cells were harvested in Tryptose Broth (TB) until a suspension with an Optical Density of 2.0 was obtained, using a spectrophotometer at wavelength of 540 nm. For challenge, preparations were made that contain the following number of cells in the final challenge-volume:

$8.3 \times 10^9$ CFU/ml BIV-AVICOR; ATCC No. PTA-3668

$2.2 \times 10^9$ CFU/ml BIV-4895; ATCC No. PTA-3667

$1.0 \times 10^{10}$ CFU/ml BIV-07990; ATCC No. PTA-3669

At 13 weeks of age, 20 vaccinated and 20 non-vaccinated birds were challenged by intravenous route of 0.2 ml of the inoculum (at least 108.0 CFU/bird). Birds were observed for 3 days for morbidity and mortality. After three days of observation all the remaining birds were sacrificed and re-isolation of the bacteria from liver and gonads were made from each bird. Post-mortem lesions of birds that died were also recorded.

Results

| Group of Birds | Challenge Inoculum | Mortality + Reisolation | Protection (%) |
|---|---|---|---|
| Control Negative Vaccinated | N/A | 0 | N/A |
| Control Negative Non-vaccinated | N/A | 0 | N/A |
| Vaccinated | ATCC No.PTA-3669 | 27.3 | 72.7 |
| Vaccinated | ATCC No.PTA-3668 | 20.9 | 79.1 |
| Vaccinated | ATCC No.PTA-3667 | 16.7 | 83.7 |
| Control Positive | ATCC No.PTA-3669 | 53.3 | 46.7 |
| Control Positive | ATCC No.PTA-3668 | 53.3 | 46.7 |
| Control Positive | ATCC No.PTA-3667 | 64.3 | 35.7 |

Serological Test

Hyperimmune sera were produced in rabbits with isolate representing each biotype, according to the method of Biberstein et. al. (Biberstein E L., Meyer M. E., and Kenedy P. C. Colonial variation of *Pasteurella* haemolytica isolated from sheep. J. Bact. 1958, 76: 445-452.)

The isolates were grown on blood agar overnight, then harvested in saline containing 0.3% formalin. The cells were washed once and adjusted to 10% transmittance at 575 nm for injection. The injections were by IV route according to the following schedule:

0.5 ml, 1.0, 2.0, 3.0, 3.0, 3.0 at 4 day intervals and all rabbits were bled 4 days after the final injection.

The hyperimmune serum was tested for their specificity using the 3 biotype strains and were reacted with homologous and heterologous rabbit antiserum (2 fold dilutions) by rapid plate agglutination.

Antiserum of each biotype was diluted until the end point was reached to determine the highest dilution that was positive.

| | Dilution ($\log^2$) Antigen Biotype 1 | | | | | | | | | | |
|---|---|---|---|---|---|---|---|---|---|---|---|
| Antiserum | 1 | 2 | 3 | 4 | 5 | 6 | 7 | 8 | 9 | 10 | 11 |
| 1 | + | + | + | + | + | + | + | + | + | + | + |
| 2 | − | − | − | − | − | − | − | − | − | − | − |
| 4 | − | − | − | − | − | − | − | − | − | − | − |

| | Dilution ($\log^2$) Antigen Biotype 4 | | | | | | | | | | |
|---|---|---|---|---|---|---|---|---|---|---|---|
| Antiserum | 1 | 2 | 3 | 4 | 5 | 6 | 7 | 8 | 9 | 10 | 11 |
| 1 | − | − | − | − | − | − | − | − | − | − | − |
| 2 | − | − | − | − | − | − | − | − | − | − | − |
| 4 | + | + | + | + | + | + | + | + | + | + | + |

| | Dilution ($\log^2$) Antigen Biotype 2 | | | | | | | | | | |
|---|---|---|---|---|---|---|---|---|---|---|---|
| Antiserum | 1 | 2 | 3 | 4 | 5 | 6 | 7 | 8 | 9 | 10 | 11 |
| 1 | − | − | − | − | − | − | − | − | − | − | − |
| 2 | + | + | + | + | + | + | + | + | + | + | + |
| 4 | − | − | − | − | − | − | − | − | − | − | − |

The biotype specific hyperimmune sera was then used as positive control in micro-plate serum agglutination test.

Example VI

Preparation of challenge strains and challenge of vaccinated and control groups.

Bacterial strains BIV-4895, ATCC No. PTA-3667, BIV-AVICOR, ATCC No. PTA-3668 and BIV-07990, ATCC No. PTA-3669, were grown on sheep blood agar for 24 hrs. at 37° C. The cells were harvested in Tryptose Broth (TB) until a suspension with an Optical Density of 2.0 was obtained, using a spectrophotometer at wavelength of 540 nm. For challenge, preparations were made that contain the following number of cells in the final challenge-volume:

$1.5 \times 10^{10}$ CFU/ml BIV-AVICOR; ATCC No. PTA-3668

$1.7 \times 10^{10}$ CFU/ml BIV-4895; ATCC No. PTA-3667

$1.6 \times 10^{10}$ CFU/ml BIV-07990; ATCC No. PTA-3669

At 13 weeks of age, 20 vaccinated and 20 non-vaccinated birds were challenged by intravenous route of 0.2 ml of the inoculum (at least $10^{8.0}$ CFU/bird). Birds were observed for 3 days for morbidity and mortality. After three days of observation all the remaining birds were sacrificed, post mortem lesions were recorded and re-isolation of the bacteria from liver, heart and gonads were made from each bird.

Results

TABLE 1

Evaluation on the effect of vaccine based on mortality and re-isolation.

| Group of birds | Challenge inoculum | Mortality + Reisolation | Protection % |
| --- | --- | --- | --- |
| Control negative non-vaccinated | N/A | N/A | N/A |
| Control Positive | BIV - 4895 | 70 | 30 |
| Control Positive | BIV - AVICOR | 80 | 20 |
| Control Positive | BIV - 07990 | 88.8 | 11.2 |
| Vaccinated | BIV - 4895 | 10 | 90 |
| Vaccinated | BIV - AVICOR | 10 | 90 |
| Vaccinated | BIV - 07990 | 15 | 85 |

TABLE 2

Evaluation on the effect of vaccine based on gross lesions following challenge.

| Group of birds | Challenge inoculum | % of Lesions | Protection % |
| --- | --- | --- | --- |
| Control negative non-vaccinated | N/A | N/A | N/A |
| Control Positive | BIV - 4895 | 74.4 | 25.6 |
| Control Positive | BIV - AVICOR | 27.0 | 73.0 |
| Control Positive | BIV - 07990 | 7.0 | 93.0 |
| Vaccinated | BIV - 4895 | 4.0 | 96.0 |
| Vaccinated | BIV - AVICOR | 1.1 | 99.0 |
| Vaccinated | BIV - 07990 | 2.4 | 98.0 |

The invention claimed is:

1. The *Gallibacterium anatis* isolate BIV-07990 deposited with the ATCC under the accession number ATCC No. PTA-3669.

2. An immunogenic composition comprising the *Gallibacterium anatis* isolate according to claim 1.

3. An immunogenic composition according to claim 2, wherein said *Gallibacterium anatis* isolate is inactivated.

4. A method of preventing an infection of the upper respiratory tract or of the reproductive tract of poultry by *Gallibacterium anatis* isolate BIV-07990 deposited with the ATCC under the accession number ATCC No. PTA-3669 comprising administering to poultry the immunogenic composition according to claim 2.

* * * * *